(12) United States Patent
Ohshima

(10) Patent No.: US 8,702,611 B2
(45) Date of Patent: Apr. 22, 2014

(54) ULTRASOUND PROBE AND ULTRASOUND DIAGNOSTIC APPARATUS

(75) Inventor: Yuji Ohshima, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 89 days.

(21) Appl. No.: 13/402,913

(22) Filed: Feb. 23, 2012

(65) Prior Publication Data

US 2012/0232397 A1 Sep. 13, 2012

(30) Foreign Application Priority Data

Mar. 11, 2011 (JP) ................................. 2011-054135

(51) Int. Cl.
*A61B 8/14* (2006.01)

(52) U.S. Cl.
USPC ........... 600/447; 600/437; 600/443; 600/444; 600/458; 600/464; 73/602

(58) Field of Classification Search
USPC .................. 600/437, 443, 447, 464; 703/602; 73/602
See application file for complete search history.

(56) References Cited

U.S. PATENT DOCUMENTS

| 2004/0015079 | A1* | 1/2004 | Berger et al. ................. 600/437 |
| 2010/0160786 | A1 | 6/2010 | Nordgren et al. |
| 2011/0077524 | A1* | 3/2011 | Oshiki et al. .................. 600/458 |
| 2011/0203374 | A1* | 8/2011 | Oshiki ............................ 73/602 |

FOREIGN PATENT DOCUMENTS

| JP | 2004-248973 | 9/2004 |
| JP | 2005-253776 | 9/2005 |
| JP | 2010-528697 | 8/2010 |
| WO | 2008/146203 | 12/2008 |
| WO | 2009/144631 | 12/2009 |

OTHER PUBLICATIONS

Official Action dated Mar. 5, 2013 issued by the Japanese Patent Office in corresponding Japanese Patent Application No. 2011-054135 with partial English translation, 7 pages.

* cited by examiner

*Primary Examiner* — Baisakhi Roy
(74) *Attorney, Agent, or Firm* — Young & Thompson

(57) ABSTRACT

The ultrasound probe includes a first priority setting unit which sets a priority regarding which of temporal resolution and spatial resolution is given preference, and a measurement parameter setting unit which sets values of measurement parameters relating to the temporal resolution and the spatial resolution in accordance with the priority set by the first priority setting unit and a measurement depth set in advance such that power consumption falls within the allowable power consumption.

16 Claims, 4 Drawing Sheets

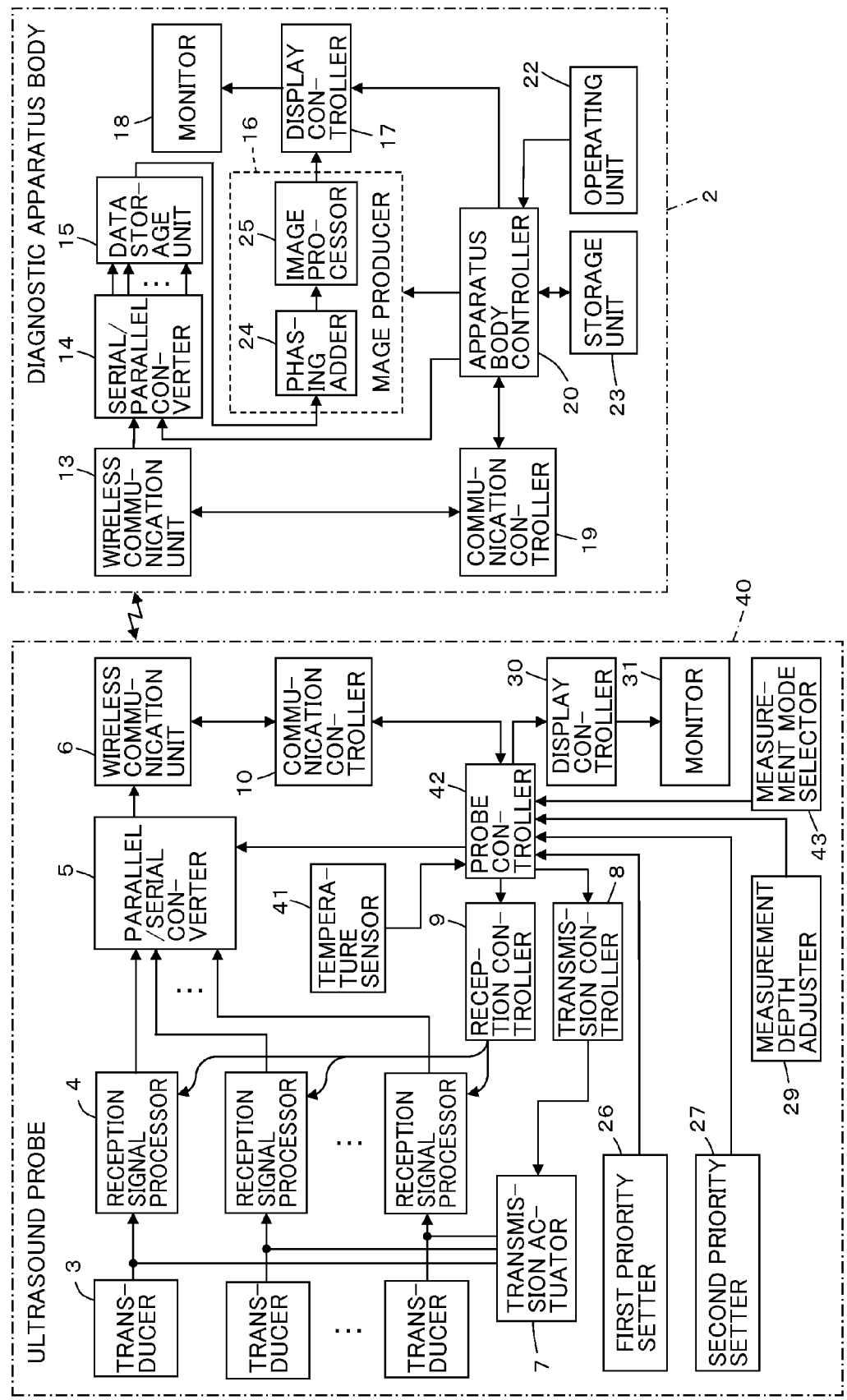

ULTRASOUND PROBE AND ULTRASOUND DIAGNOSTIC APPARATUS

BACKGROUND OF THE INVENTION

1. Field of the Invention

The present invention relates to an ultrasound probe which performs transmission and reception of ultrasonic waves, and to an ultrasound diagnostic apparatus which performs transmission and reception of ultrasonic waves to produce an ultrasound image.

2. Description of the Related Art

An ultrasound diagnostic apparatus using an ultrasound image has hitherto been put into practical use in the field of medicine. In general, this kind of ultrasound diagnostic apparatus has an ultrasound probe embedded with a transducer array and an ultrasound diagnostic apparatus body connected to the ultrasound probe. An ultrasonic wave is transmitted from the ultrasound probe toward a subject, an ultrasonic echo signal from the subject is received by the ultrasound probe, and the reception signal is electrically processed in the ultrasound diagnostic apparatus body to produce an ultrasound image.

In recent years, in order to improve convenience of an operator, such as a technician, the provision of various switches has been considered in the ultrasound probe to control the operation of the ultrasound diagnostic apparatus. For example, JP 2004-248973 A describes a technique in which an imaging plane is appropriately switched by a selection switch provided in a hand grip of the ultrasound probe without touching the ultrasound diagnostic apparatus body.

In general, the ultrasound probe uses a piezoelectric device as an ultrasound transducer which transmits and receives an ultrasonic wave. When transmitting an ultrasonic wave, an activation signal having a large amount of energy is supplied to the ultrasound transducer. However, the entire amount of energy of the activation signal is not converted to ultrasonic energy in the ultrasound transducer, and some amount of energy is converted to heat. For this reason, the ultrasound transducer generates heat. In a transmission/reception control circuit which is used for transmission and reception of an ultrasonic wave by the ultrasound transducer, the activation signal is converted to heat. Accordingly, when transmission of an ultrasonic wave is performed by the ultrasound transducer, the entire ultrasound probe increases in temperature. Since the ultrasound probe is used in a state of being in contact with a biological body, such as a human body, from the viewpoint of low-temperature burn prevention or the like, the surface temperature is limited and should be equal to or lower than 43° C.

In the ultrasound diagnostic apparatus which is usually used for medical treatment or medical examination in a hospital, the ultrasound diagnostic apparatus body and the ultrasound probe are connected through a cable. In recent years, in order to remove the burden of the cable and to improve convenience of the operator, in particular, in a portable ultrasound diagnostic apparatus which is usable outside, such as a disaster area, not inside, such as a hospital, a wireless probe has been developed in which wireless communication is performed between the ultrasound diagnostic apparatus body and the ultrasound probe. The wireless probe should be provided with various circuits for wireless communication therein along with the ultrasound transducer. Accordingly, in the wireless probe, heat is more likely to be generated compared to a general ultrasound probe with cable connection.

In order to prevent heat generation of the ultrasound probe, an increase in the surface area of the ultrasound probe or the provision of a cooling mechanism in the ultrasound probe has been considered. However, it is preferable that the ultrasound probe is of small size. The smaller the size of the ultrasound probe, the smaller the surface area. For this reason, there is a problem in that the heat dissipation area decreases, and the ability to radiate heat generated from the ultrasound transducer or an internal circuit is insufficient. There is also a problem in that, as the ultrasound probe is of small size, it is difficult to secure the space where the cooling mechanism is mounted.

As another method which prevents heat generation of the ultrasound probe, suppression of power consumption in the ultrasound probe has been considered. JP 2005-253776 A describes an ultrasound diagnostic apparatus which automatically changes the activation condition of the ultrasound transducer in accordance with the surface temperature of the ultrasound probe so as to prevent the surface of the ultrasound probe from reaching at high temperature.

On the other hand, in the apparatus described in JP 2004-248973 A, when a puncture guideline at the time of insertion of a puncture needle is displayed, even if the operator unintentionally touches the switch of the ultrasound probe, the operation of the switch of the ultrasound probe is limited such that an imaging plane where the image of the puncture needle is detectable is not switched to another imaging plane where the image of the puncture needle is not viewed. In this case, there is a problem in that heat generation in the ultrasound transducer, the transmission/reception control circuit, or the like, in particular, heat generation in the wireless probe is not taken into consideration.

In the apparatus described in JP 2005-253776 A, the value, such as a frame rate, is primarily determined in accordance with the surface temperature of the ultrasound probe, or the like. Accordingly, there is a problem in that a desirable ultrasound image for the operator may not be obtained.

SUMMARY OF THE INVENTION

The invention has been finalized in consideration of the above-described situation, and an object of the invention is to provide an ultrasound probe and an ultrasound diagnostic apparatus capable of allowing an operator to set whether to obtain an ultrasound image having preference on a frame rate or to obtain an ultrasound image having preference on image quality in accordance with a site under diagnosis or a diagnosis object while suppressing power consumption in the ultrasound probe to be equal to or lower than allowable power consumption to suppress heat generation to be equal to or smaller than a threshold value, and obtaining an ultrasound image for diagnosis having a desired frame rate and/or desired image quality as the operator desires.

An ultrasound probe according to the present invention is an ultrasound probe which transmits a transmission signal produced through a signal process on a reception signal, which is acquired by transmitting ultrasonic waves toward a subject and receiving an ultrasonic echo reflected from a measurement site of the subject, to an apparatus body of an ultrasound diagnostic apparatus, which produces an ultrasound diagnostic image from the transmission signal, the ultrasound probe comprising a first priority setting unit which sets a first priority regarding which of a first measurement parameter relating to temporal resolution and a second measurement parameter relating to spatial resolution when acquiring the reception signal to produce the ultrasound diagnostic image is given preference; a measurement parameter setting unit which sets values of the first and second measurement parameters in accordance with allowable power consumption set in advance in accordance with heat generation associated with a process including the signal process, a measurement depth set in accordance with the measurement site of the subject, and the first priority set by the first priority setting unit; and an operation control unit which controls transmission and reception operations based on the first and second measurement parameters set by the measurement parameter setting unit.

Preferably, the measurement parameter setting unit sets the values of the first and second measurement parameters in accordance with the measurement depth and the first priority such that power consumption falls within the allowable power consumption.

Preferably, the first measurement parameter is a frame rate when acquiring the reception signal to produce the ultrasound diagnostic image, and the second measurement parameter is the number of scan lines for producing the ultrasound diagnostic image and the number of channels of transmission and reception of the ultrasonic waves.

Preferably, the ultrasound probe according to the present invention further comprises a second priority setting unit which sets a second priority regarding which of the number of scan lines and the number of channels included in the second measurement parameter relating to the spatial resolution is given preference, wherein the measurement parameter setting unit sets values of the number of scan lines and the number of channels in accordance with a set value of the second measurement parameter and the second priority set by the second priority setting unit.

Alternatively, the ultrasound probe according to the present invention preferably further comprises a monitor which displays at least one of the first measurement parameter, the second measurement parameter, the measurement depth, the frame rate, the number of scan lines, and the number of channels.

Preferably, the ultrasound probe according to the present invention further comprises an adjustment amount setting unit which, with the measurement depth set in advance for the measurement site of the subject as an initial depth, sets an adjustment amount to adjust the measurement depth to a deeper side than the initial depth or an adjustment amount to adjust the measurement depth to a shallower side than the initial depth, wherein the measurement parameter setting unit further sets the adjusted measurement depth in accordance with the initial depth set in advance and the adjustment amount set by the adjustment amount setting unit.

Preferably, the priority setting unit is a rotating dial.

Preferably, the ultrasound probe according to the present invention further comprises a grip portion which is gripped by an operator and a head portion which abuts on the subject and irradiates the ultrasonic waves, wherein the priority setting unit is provided at a position, excluding the grip portion and the head portion, at which the operator does not grip.

Preferably, the ultrasound probe according to the present invention further comprises a measurement mode selecting unit which selects a measurement mode of the subject. Preferably, the measurement mode includes a mode in which at least one measurement site is measured and/or a still image of the ultrasound diagnostic image is produced.

Preferably, the ultrasound probe according to the present invention further comprises a temperature sensor which measures an internal temperature or a surface temperature of the ultrasound probe and an allowable value setting unit which changes a value of the allowable power consumption set in advance based on the internal temperature or the surface temperature measured by the temperature sensor.

An ultrasound diagnostic apparatus according to the present invention comprises the above ultrasound probe and an ultrasound diagnostic apparatus body which produces an ultrasound diagnostic image, wherein the ultrasound probe further includes an ultrasound transmitting/receiving unit which transmits the ultrasonic waves toward the subject, receives the ultrasonic echo reflected from the subject, and outputs the reception signal, a signal processor which performs the signal process on the reception signal output from the ultrasound transmitting/receiving unit to produce the transmission signal, and a first communication unit which transmits the transmission signal produced by the signal processor to the ultrasound diagnostic apparatus body which produces the ultrasound diagnostic image from the transmission signal, and wherein the ultrasound diagnostic apparatus body includes a second communication unit which receives the transmission signal from the first communication unit of the ultrasound probe, an image producer which produces the ultrasound diagnostic image based on the transmission signal received by the second communication unit, and a monitor which displays the ultrasound diagnostic image produced by the image producer.

Preferably, the ultrasound probe further comprises a first wireless communication unit which transmits the transmission signal to the ultrasound diagnostic apparatus body in a wireless manner, wherein the first communication unit is the first wireless communication unit which transmits the transmission signal to the ultrasound diagnostic apparatus body in a wireless manner, and wherein the second communication unit is a second wireless communication unit which receives the transmission signal from the first wireless communication unit of the ultrasound probe in a wireless manner.

Preferably, the monitor of the ultrasound diagnostic apparatus body displays at least one of the measurement depth, the first measurement parameter, the second measurement parameter, a frame rate as the first measurement parameter, and the number of scan lines and the number of channels included in the second measurement parameter.

Further, an ultrasound diagnostic apparatus according to the present invention comprises an ultrasound diagnostic apparatus body which produces an ultrasound diagnostic image and an ultrasound probe which transmits and receives ultrasonic waves to produce the ultrasound diagnostic image, wherein the ultrasound probe includes an ultrasound transmitting/receiving unit which transmits the ultrasonic waves toward a subject, receives an ultrasonic echo reflected from the subject, and outputs a reception signal, a signal processor which performs a signal process on the reception signal output from the ultrasound transmitting/receiving unit to produce a transmission signal, a first priority setting unit which sets a first priority regarding which of a first measurement parameter relating to temporal resolution and a second measurement parameter relating to spatial resolution when acquiring the reception signal to produce the ultrasound diagnostic image is given preference, an operation control unit which controls operations of the ultrasound transmitting/receiving unit, and a first communication unit which transmits the transmission signal produced by the signal processor and the first priority set by the first priority setting unit to the ultrasound diagnostic apparatus body, and receives data from the ultrasound diagnostic apparatus body; wherein the ultrasound diagnostic apparatus body includes a second communication unit which receives the transmission signal and the first priority from the first communication unit of the ultrasound probe, and transmits data to the first communication unit of the ultrasound probe, an image producer which produces the ultrasound diagnostic image based on the transmission signal received by the second communication unit, a monitor which displays the ultrasound diagnostic image produced by the image producer, a measurement parameter setting unit for setting values of the first and second measurement parameters in accordance with the first priority set by the first priority setting unit of the ultrasound probe and received by the second communication unit, allowable power consumption set in advance in accordance with heat generation associated with the operation of the ultrasound probe, and a measurement depth set in accordance with the measurement site of the subject by the ultrasound probe; wherein the second communication unit of the ultrasound diagnostic apparatus body transmits the values of the first and second measurement parameters set by the measurement parameter setting unit to the first communication unit of the ultrasound probe as data, the first communication unit of the ultrasound probe receives the values of the first and second measurement parameters as data; and wherein the operation control unit of the ultrasound probe controls the operation of the ultrasound transmitting/receiving unit of the ultrasound probe based on the values of the first and second measurement parameters received by the first communication unit and set by the measurement parameter setting unit.

Preferably, the first communication unit of the ultrasound probe and the second communication unit of the ultrasound diagnostic apparatus body are wireless communication units which perform wireless communication.

The present invention enables the operator to set a desired frame rate and/or desired image quality while suppressing power consumption in the ultrasound probe to an allowable power consumption or less and suppressing heat generation to a threshold or less and obtain an optimum diagnostic image for the operator from the viewpoint of a frame rate and/or image quality.

BRIEF DESCRIPTION OF THE DRAWINGS

FIG. 3 is a block diagram showing the configuration of an ultrasound diagnostic apparatus according to Embodiment 2 of the invention.

DETAILED DESCRIPTION OF THE INVENTION

Hereinafter, an ultrasound probe and an ultrasound diagnostic apparatus according to the invention will be described in detail on the basis of preferred embodiments shown in the accompanying drawings.

Embodiment 1

Figure 1:
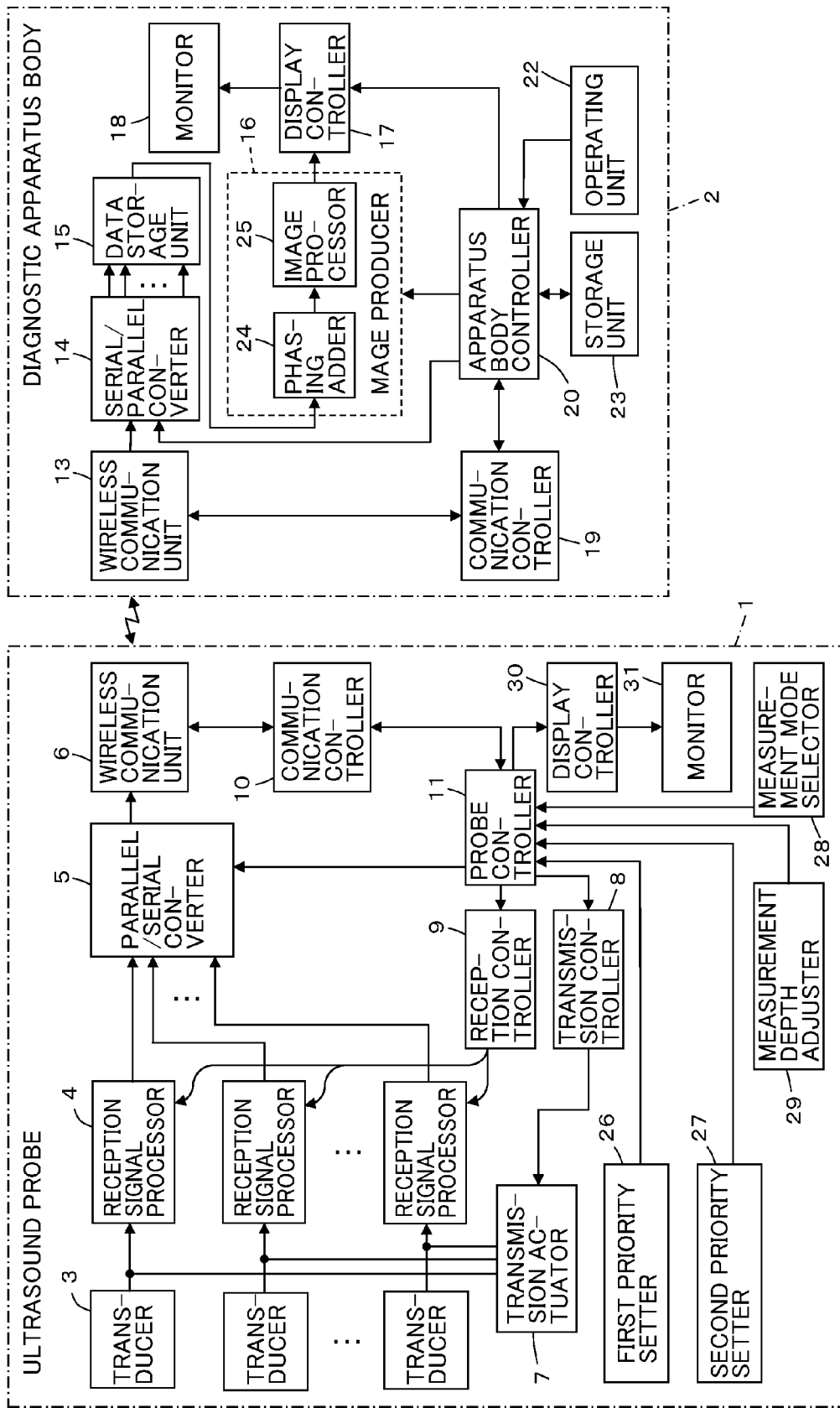
FIG. 1 is a block diagram showing the configuration of an ultrasound diagnostic apparatus according to Embodiment 1 of the invention.

FIG. 1 is a block diagram showing an example of the configuration of an ultrasound diagnostic apparatus according to Embodiment 1 of the invention.

As shown in FIG. 1, the ultrasound diagnostic apparatus of this embodiment includes an ultrasound probe 1, and an ultrasound diagnostic apparatus body 2 which performs communication with the ultrasound probe 1 through wireless communication.

The ultrasound probe 1 is pushed and abutted on a subject to transmit ultrasonic waves toward a target site of the subject, and receives an ultrasonic echo from the target site of the subject to acquire ultrasound image information relating to the target site. As shown in FIG. 1, the ultrasound probe 1 has a plurality of ultrasound transducers 3 constituting a one-dimensional or two-dimensional transducer array, a plurality of reception signal processors 4 which are provided to correspond to the transducers 3, a parallel/serial converter 5, a wireless communication unit 6, a transmission drive 7, a transmission controller 8, a reception controller 9, a communication controller 10, a probe controller 11, a first priority setter 26, a second priority setter 27, a measurement depth adjuster 28, a measurement mode selector 29, a display controller 30, and a monitor 31.

A plurality of transducers 3 transmit ultrasonic waves in response to an activation signal supplied from the transmission drive 7, receives an ultrasonic echo from the subject, and outputs a reception signal to the reception signal processor 4. Each transducer 3 is constituted by a vibrator in which electrodes are formed at both ends of a piezoelectric body made of piezoelectric ceramic represented by PZT (Pb (lead) zirconate titanate) or a polymer piezoelectric device represented by PVDF (polyvinylidene difluoride).

If a pulsed or continuous-wave voltage is applied across the electrodes of the vibrator, the piezoelectric body expands and contracts. Then, pulsed or continuous-wave ultrasonic waves are produced from the vibrators and synthesized to form an ultrasonic beam. When receiving the propagating ultrasonic waves, the vibrators expand and contract to produce electric signals, and the electric signals are output as the reception signals of the ultrasonic waves.

The transmission drive 7 includes, for example, a plurality of pulsars. The transmission drive 7 adjusts the delay amount of each of the activation signals on the basis of a transmission delay pattern selected by the transmission controller 8 such that ultrasonic waves transmitted from a plurality of transducers 3 form a wide ultrasonic beam which covers an area of a tissue in the subject, and supplies the activation signals to a plurality of transducers 3.

The reception signal processor 4 of each channel performs an orthogonal detection process or an orthogonal sampling process on the reception signal output from the corresponding transducer 3 under the control of the reception controller 9 to produce a complex baseband signal, samples the complex baseband signal to produce sample data including information regarding an area of a tissue, and supplies sample data to the parallel/serial converter 5. The reception signal processor 4 may perform data compression for high-efficiency encoding on data obtained by sampling the complex baseband signal to produce sample data.

The parallel/serial converter 5 converts parallel sample data produced by a plurality of channels of reception signal processors 4 to serial sample data.

The wireless communication unit 6 modulates a carrier on the basis of serial sample data to produce a transmission signal, supplies the transmission signal to an antenna, and transmits a radio wave from the antenna to transmit serial sample data. As the modulation system, for example, ASK (Amplitude Shift Keying), PSK (Phase Shift Keying), QPSK (Quadrature Phase Shift Keying), 16QAM (16 Quadrature Amplitude Modulation), or the like is used.

The wireless communication unit 6 performs wireless communication with the ultrasound diagnostic apparatus body 2 to transmit sample data to the ultrasound diagnostic apparatus body 2, receives various control signals from the ultrasound diagnostic apparatus body 2, and outputs the received control signals to the communication controller 10.

The communication controller 10 controls the wireless communication unit 6 such that the transmission of sample data is performed with transmission radio field intensity set by the probe controller 11, and outputs various control signals received by the wireless communication unit 6 to the probe controller 11.

The first priority setter 26 is an exceedingly characteristic portion of the invention, and sets a priority regarding which of a measurement parameter relating to temporal resolution, such as a frame rate, and a measurement parameter relating to spatial resolution, such as the number of lines and the number of channels, is given preference.

The second priority setter 27 is also an exceedingly characteristic portion of the invention, and sets a priority regarding which of the number of lines and the number of channels from the measurement parameter relating to spatial resolution according to the priority set by the first priority setter 26 is given preference.

The details and the setting operations of the first priority setter 26 and the second priority setter 27 will be described below.

The measurement mode selector 28 can select a measurement mode according to a measurement site of the subject, such as heart, liver, or stomach, or a measurement mode, such as still image acquisition. If a measurement mode is selected by the measurement mode selector 28, the probe controller 11 sets a measurement depth and a measurement parameter to a default value (a measurement parameter set by default), which is set in the selected measurement mode, in accordance with the selected measurement mode. For example, if a site to be measured is selected by the measurement mode selector 28, the measurement depth is determined as a default value (initial depth).

The measurement depth adjuster 29 can adjust the measurement depth (initial depth) of the default value set in accordance with the measurement mode selected by the measurement mode selector 28.

The probe controller 11 controls the respective units of the ultrasound probe 1, for example, the parallel/serial converter 5, the transmission controller 8, the reception controller 9, the communication controller 10, the display controller 30, and the like on the basis of various control signals transmitted from the ultrasound diagnostic apparatus body 2 or signals from the first priority setter 26, the second priority setter 27, the measurement depth adjuster 28, and the measurement mode selector 29.

The probe controller 11 has an internal memory (not shown), and stores, in the internal memory, a relational expression or a table regarding the possible values of the measurement parameter relating to temporal resolution and the measurement parameter relating to spatial resolution for the measurement depth, specifically, a relationship expression or a table regarding the possible values of the measurement depth, the frame rate, the number of lines, and the number of channels. The relational expression or the table, for example, an LUT (Look-Up Table) is used to obtain the possible values of the measurement depth, the frame rate of the measurement parameter relating to temporal resolution, and the number of lines and the number of channels of the measurement parameter relating to spatial resolution set in accordance with the measurement mode to suppress heat generation in the ultrasound probe 1 to be equal to or smaller than a threshold value because the surface temperature of the ultrasound probe 1 is limited to be equal to or lower than a predefined value, specifically, in a range in which the total power consumption by the operation of the ultrasound probe 1 falls within an upper limit value, that is, to be equal to or lower than allowable power consumption.

The probe controller 11 stores, in the internal memory, the set values of the measurement parameters, such as the measurement depth, the frame rate, the number of lines, and the number of channels set by default, for each measurement mode.

In the invention, the probe controller 11 suppresses power consumption in the ultrasound probe 1 to be equal to or lower than allowable power consumption on the basis of the priorities set by the first priority setter 26 and the second priority setter 27, sets the measurement parameter relating to temporal resolution and the measurement parameter relating to spatial resolution while suppressing heat generation to be equal to or smaller than the threshold value, finally, the measurement parameters, such as frame rate, the number of lines, and the number of channels, and controls the respective units of the ultrasound probe 1 in accordance with the set measurement parameters.

In the invention, the probe controller 11 suppresses power consumption in the ultrasound probe 1 to be equal to or lower than allowable power consumption on the basis of the priorities set by the first priority setter 26 and the second priority setter 27, sets the measurement parameters, such as the frame rate as the measurement parameter relating to temporal resolution, and the number of lines and the number of channels as the measurement parameter relating to spatial resolution, while suppressing heat generation to be equal to or smaller than the threshold value, and controls the respective units of the ultrasound probe 1 in accordance with the set measurement parameter.

The probe controller 11 sets the measurement depth, the measurement parameter, or the like to the default value of each measurement mode on the basis of the measurement mode selected by the measurement mode selector 29, and controls the respective units of the ultrasound probe 1 in accordance with the set measurement parameter.

The probe controller 11 controls the measurement depth by the ultrasound probe 1 (a plurality of ultrasound transducers 3) in accordance with the adjustment amount by the measurement depth adjuster 28.

The display controller 30 is controlled by the probe controller 11, and displays information of the set measurement parameter, measurement depth, or the like on the monitor 31.

The monitor 31 includes, for example, a display device, such as an LCD, and displays the measurement parameter, the measurement depth, or the like under the control of the display controller 30.

The ultrasound probe 1 may be an external probe, such as a linear scan system, a convex scan system, or a sector scan system, or a probe for an ultrasound endoscope, such as a radial scan system. The respective units of the ultrasound probe 1 are powered by a battery (not shown).

The ultrasound probe 1 is basically configured as described above.

As shown in FIG. 1, the ultrasound diagnostic apparatus body 2 has a wireless communication unit 13, a serial/parallel converter 14, a data storage unit 15, an image producer 16, a display controller 17, a monitor 18, a communication controller 19, an apparatus body controller 20, an operating unit 22 which is used when the operator performs an input operation, and a storage unit 23 which stores an operation program.

The wireless communication unit 13 performs wireless communication with the wireless communication unit 6 in the ultrasound probe 1 to transmit various control signals to the ultrasound probe 1. The wireless communication unit 13 receives and demodulates signals transmitted from the wireless communication unit 6 to output serial sample data.

The communication controller 19 controls the wireless communication unit 13 such that the transmission of various control signals and the reception of sample data are performed with transmission radio field intensity set by the apparatus body controller 20.

The serial/parallel converter 14 is controlled by the apparatus body controller 20, and converts serial sample data output from the wireless communication unit 13 to parallel sample data.

The data storage unit 15 is constituted by a memory, a hard disk, or the like, and stores sample data for at least one frame converted by the serial/parallel converter 14.

The image producer 16 is controlled by the apparatus body controller 20, and performs a reception focus process on sample data for each frame read from the data storage unit 15 to produce an image signal representing an ultrasound image. The image producer 16 includes a phasing adder 24 and an image processor 25.

The phasing adder 24 performs a reception focus process for selecting one reception delay pattern from among a plurality of reception delay patterns stored in advance in accordance with the reception direction set in the apparatus body controller 20, giving a delay to each of a plurality of complex baseband signals represented by sample data on the basis of the selected reception delay pattern, and adding the complex baseband signals. With this reception focus process, the focus of an ultrasonic echo is narrowed to produce a baseband signal (sound ray signal).

The image processor 25 produces a B-mode image signal which is tomographic image information relating to the tissue of the subject on the basis of the sound ray signal produced by the phasing adder 24. The image processor 25 includes an STC (sensitivity time control) unit and a DSC (digital scan converter). The STC unit corrects attenuation depending on the distance in accordance with the depth of the reflection position of the ultrasonic wave for the sound ray signal. The DSC converts (raster-converts) the sound ray signal corrected by the STC unit to an image signal based on a normal television signal scan system, and performs a necessary image process, such as a gradation process, to produce a B-mode image signal.

The display controller 17 is controlled by the apparatus body controller 20, and displays an ultrasound diagnostic image on the monitor 18 on the basis of the image signal produced by the image producer 16.

The monitor 18 includes, for example, a display, such as an LCD, and displays an ultrasound diagnostic image under the control of the display controller 17.

The apparatus body controller 20 controls the respective units of the ultrasound diagnostic apparatus body 2, for example, the serial/parallel converter 14, the image producer 16, the display controller 17, the communication controller 19, the storage unit 23, and the like on the basis of an input signal from the operating unit 22.

In this ultrasound diagnostic apparatus body 2, the serial/parallel converter 14, the image producer 16, the display controller 17, the communication controller 19, and the apparatus body controller 20 may be constituted by a CPU and an operation program which causes the CPU to perform various processes. A part or the whole of the apparatus body controller 20 may be constituted by digital circuits.

The storage unit 23 stores various kinds of information or programs for activating and controlling the ultrasound diagnostic apparatus including the ultrasound diagnostic apparatus body 2 and the ultrasound probe 1. Accordingly, the operation program is stored in the storage unit 23.

As a storage medium in the storage unit 23, in addition to an embedded hard disk, a flexible disk, an MO, an MT, a RAM, a CD-ROM, a DVD-ROM, or the like may be used.

The ultrasound diagnostic apparatus body 2 is basically constituted as described above.

Subsequently, the structure of the ultrasound probe 1 of the ultrasound diagnostic apparatus of this embodiment shown in FIG. 1 will be described with reference to FIGS. 2A to 2E.

Figure 2A:
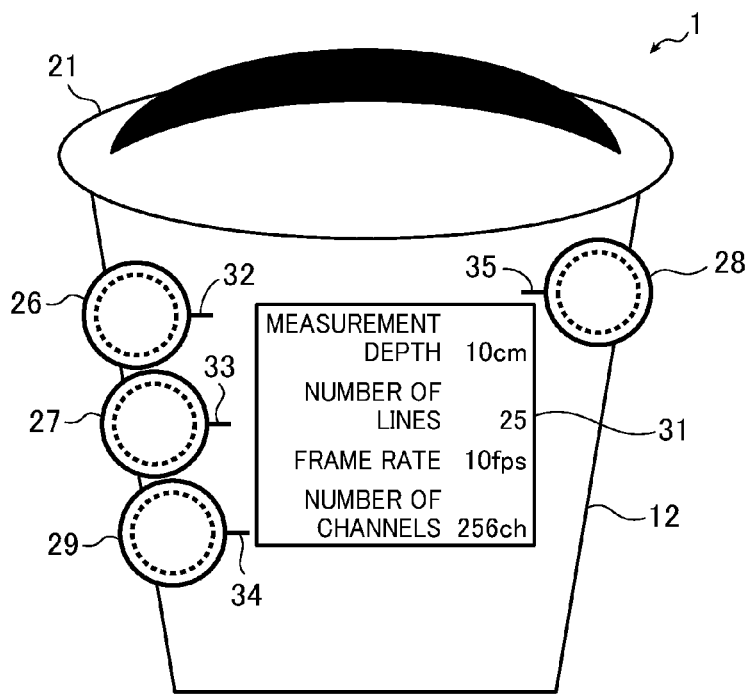
FIG. 2A is an appearance diagram of an ultrasound probe of the ultrasound diagnostic apparatus shown in FIG. 1, and FIGS. 2B, 2C, 2D, and 2E are enlarged views of a first priority setter, a second priority setter, a measurement depth adjuster, and a measurement mode selector of the ultrasound probe shown in FIG. 2A.

FIG. 2A is an appearance diagram of the ultrasound probe 1 shown in FIG. 1. As shown in FIG. 2A, the ultrasound probe 1 has a grip portion 12 and a head portion 21. The grip portion 12 is provided with a first priority setter 26, a second priority setter 27, a measurement mode selector 28, a measurement depth adjuster 29, and a monitor 31. The head portion 21 includes the transducers 3 (see FIG. 1), and the transducers 3 transmit ultrasonic waves from the head portion 21.

As shown in FIG. 2A, the first priority setter 26, the second priority setter 27, the measurement mode selector 28, and the measurement depth adjuster 29 are rotating dials, and are rotatably provided on the surface of the grip portion 12. In the example of the drawing, the first priority setter 26, the second priority setter 27, and the measurement depth adjuster 29 are provided on the surface of the grip portion 12 in line near the left side of the drawing. Since these are likely to be simultaneously operated by the operator, if disposed nearby, ease of operation is achieved. The measurement mode selector 28 is provided on the right side of the drawing at a distance from the first priority setter 26 and the like.

In the invention, the first priority setter 26, the second priority setter 27, the measurement mode selector 28, and the measurement depth adjuster 29 are not limited to the positions of the example of the drawing, and may be provided at any positions. It is preferable that these are provided at positions which are not touched when the operator grips the grip portion 12.

The monitor 31 is provided on the surface of the grip portion 12 and at a position not overlapping the first priority setter 26, the second priority setter 27, the measurement mode selector 28, and the measurement depth adjuster 29. The monitor 31 displays parameters relating to measurement, and for example, the measurement depth, the frame rate, the number of lines, the number of channels, and the like are displayed. The frame rate is the number of screens which are updated per unit time of a moving image displayed on the screen of the monitor 18 of the ultrasound diagnostic apparatus body 2. The number of lines is the number of scan lines constituting an ultrasound image. The number of channels is the number of transducers which are used to acquire one scan line. The operator views the monitor 31 to confirm the current measurement parameters. It is not necessary for all of the measurement parameters to be displayed on the monitor 31, and only the measurement parameters desired by the operator may be displayed.

Figure 2B:
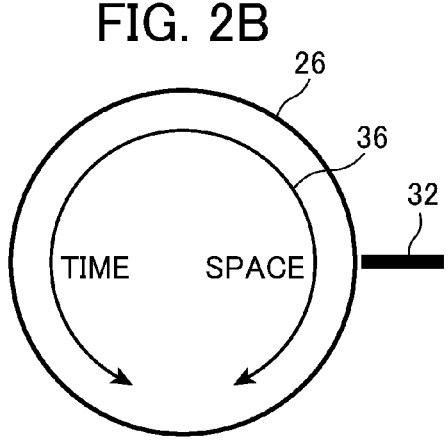

FIG. 2B is an enlarged view of the first priority setter 26 of the ultrasound probe 1 shown in FIG. 2A.

The first priority setter 26 is an input device which sets a priority regarding which of temporal resolution and spatial resolution is given preference. A double-headed arrow 36 is drawn on the surface of the first priority setter 26 along the outer periphery of the first priority setter 26. Characters of time and space are drawn in the vicinity of the tips of the double-headed arrow 36. The character of time represents temporal resolution, and the character of space represents spatial resolution. The measurement parameter relating to temporal resolution is exemplified by the frame rate. The measurement parameter relating to spatial resolution is exemplified by the number of lines and the number of channels (the number of CH). The double-headed arrow 36 and the characters show that, if the first priority setter 26 is rotated to the left with respect to the grip portion 12, spatial resolution is given preference, and if the first priority setter 26 is rotated to the right, temporal resolution is given preference. The position of a scale 32 represents the current priority.

That is, the operator adjusts the direction of the first priority setter 26 with respect to the scale 32 drawn on the surface of the grip portion 12 in accordance with the preference of the operator, or the like, regarding a need as a diagnostic image, screening or strict observation, that is, whether the whole needs to be diagnosed or a predetermined site is approached and needs to be diagnosed while viewing the ultrasound diagnostic image displayed on the monitor 18 of the ultrasound diagnostic apparatus body 2, thereby setting which of temporal resolution and spatial resolution is given preference and the priority. For example, if the first priority setter 26 is rotated to the right with respect to the grip portion 12, and the left end of the double-headed arrow 36 and the position of the scale 32 are aligned, a setting is made such that temporal resolution is given most preference. If the midpoint of the double-headed arrow 36 and the position of the scale 32 are aligned, a setting is made such that temporal resolution and spatial resolution have the same priority. The priority set by the first priority setter 26 is output to the probe controller 11.

Figure 2C:
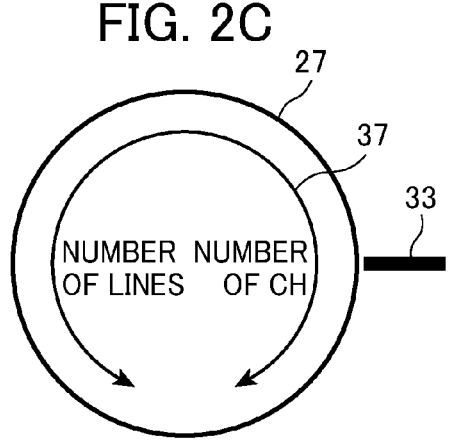

FIG. 2C is an enlarged view of the second priority setter 27 of the ultrasound probe 1 shown in FIG. 2A.

The second priority setter 27 sets which of the number of lines and the number of channels is given preference. Similarly to the first priority setter 26, a double-headed arrow 37 is drawn on the surface of the second priority setter 27. Characters of the number of lines and the number of CHs are drawn in the vicinity of the tips of the double-headed arrow 37. The double-headed arrow 37 and the characters represent that, if the second priority setter 27 rotates to the left with respect to the grip portion 12, the number of channels is given preference, and if the second priority setter 27 rotates to the right, the number of lines is given preference.

That is, the operator adjusts the direction of the second priority setter 27 with respect to a scale 33 drawn on the surface of the grip portion 12 in accordance with a need as a diagnostic image, the preference of the operator, or the like while viewing the ultrasound diagnostic image displayed on the monitor 18 of the ultrasound diagnostic apparatus body 2, thereby setting which of the number of lines and the number of channels from among the measurement parameters relating to spatial resolution is given preference and the priority. The priority set by the second priority setter 27 is output to the probe controller 11.

The probe controller 11 suppresses power consumption in the ultrasound probe 1 at the currently set measurement depth to be equal to or lower than allowable power consumption in accordance with the priorities set by the first priority setter 26 and the second priority setter 27, and sets the values of the frame rate, the number of channels, and the number of lines while suppressing heat generation to be equal to or smaller than a threshold value.

The probe controller 11 controls the operations of the respective units of the ultrasound probe 1 in accordance with the set frame rate, the number of channels, and the number of lines.

Figure 2D:
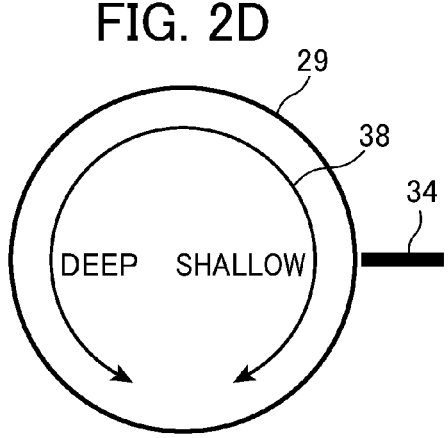

FIG. 2D is an enlarged view of the measurement depth adjuster 29 of the ultrasound probe 1 shown in FIG. 2. The measurement depth adjuster 29 is used to adjust the measurement depth by the ultrasound probe 1 in the ultrasound diagnostic apparatus with respect to the currently set measurement depth (initial depth).

Similarly to the first priority setter 26, a double-headed arrow 38 is drawn on the surface of the measurement depth adjuster 29. Characters representing "deep" and "shallow" are indicated in the vicinity of the tips of the double-headed arrow 38. The double-headed arrow 38 and the characters show that, if the measurement depth adjuster 29 is rotated to the left with respect to the grip portion 12, the measurement depth is set to be shallow, and if the measurement depth adjuster 29 rotates to the right, the measurement depth is set to be deep. The position of a scale 34 represents the priority of the measurement depth.

That is, when, for example, the operator, viewing the ultrasound diagnostic image displayed on the monitor 18 of the ultrasound diagnostic apparatus body 2, finds that the measurement depth (initial depth), which is currently set for a measurement target, e.g., a measurement depth which is set by default for a measurement target in accordance with the measurement mode and at which observation is currently being performed, does not register with the measurement target, or the like, and when the operator desires to make an adjustment, be it slight or fine, according to the measurement target, the operator may adjust the measurement depth by adjusting the direction of the measurement depth adjuster 29 with respect to the scale 34 indicated on the surface of the grip portion 12. The measurement depth set by the measurement depth adjuster 29 is output to the probe controller 11.

The probe controller 11 controls the operations of the respective units of the ultrasound probe 1 in accordance with the adjusted measurement depth.

Figure 2E:
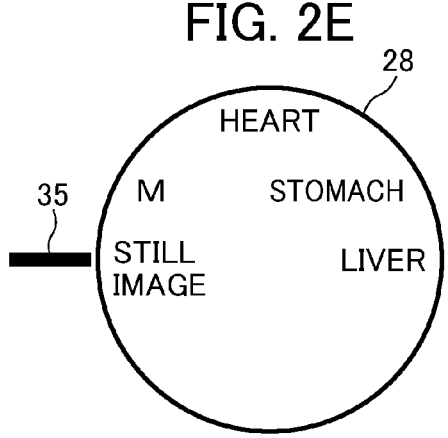

FIG. 2E is an enlarged view of the measurement mode selector 28 of the ultrasound probe shown in FIG. 2A. The names of respective modes are indicated on the surface of the measurement mode selector 28 at regular intervals. With regard to the names indicated on the surface of the measurement mode selector 28, "still image" represents a still image mode, "M" represents a manual mode, "heart" represents a heart mode, "stomach" represents a stomach mode, and "liver" represents a liver mode. The measurement mode selector 28 rotates with respect to the grip portion 12, and the name of each mode and the position of the scale 35 are aligned to select a measurement mode. For example, FIG. 2E shows a case where the still mode is selected as a measurement mode. The measurement mode selected by the measurement mode selector 28 is output to the probe controller 11.

The probe controller 11 sets the measurement depth of the measurement target to the measurement depth which is set by default for the selected measurement mode, and sets the values of the frame rate, the number of channels, and the number of lines to default values.

Although only still image, manual, heart, stomach, and liver are described as the measurement mode selected by the measurement mode selector 28, the selectable measurement modes are not limited to these modes, and any measurement mode may be selected.

As the ultrasound probe 1, a dedicated ultrasound probe for a specific site determined for each measurement target site of the subject may be used. In this case, the above-described measurement mode selector 28 may not be provided because the values of the measurement depth, the frame rate, the number of channels, and the number of lines are set in advance as default values in the dedicated ultrasound probe for a specific site.

For example, if a measurement site, such as heart, is selected by the measurement mode selector 28 as the measurement mode, the measurement depth is determined and set to the default, an approximate value. The default value of the measurement depth can be, for example, 15 cm in the heart mode and 20 cm in the liver mode. Although the measurement depth is set to the default, an approximate value, depending on a measurement site, even when the measurement site is the same, the measurement depth slightly differs depending on a subject and a measurement target. Accordingly, in the invention, the measurement depth adjuster 29 is configured to perform fine adjustment of the measurement depth. For example, with regard to the measurement depth 15 cm, to which the default is set in the heart mode, the measurement depth can be adjusted in a range of −100 mm to +100 mm with 1 mm increments.

The manual mode M is the mode in which the operator can freely set the frame rate, the number of channels, and the number of lines. However, from the viewpoint of power consumption, the settable values of the frame rate, the number of channels, and the number of lines are limited, and the upper limit values thereof are determined in advance.

In the manual mode M, the operator may input the frame rate, the number of channels, and the number of lines from the operating unit 22 of the ultrasound diagnostic apparatus body 2, communication may be performed from the ultrasound diagnostic apparatus body 2 to the ultrasound probe 1, and the frame rate, the number of channels, and the number of lines may be set in the probe controller 11 of the ultrasound probe 1. However, it is preferable that the frame rate, the number of channels, and the number of lines which may not be set in the probe controller 11 may not be input from the operating unit 22.

In the manual mode M, similarly to the frame rate, the number of channels, and the number of lines, the measurement depth may be set.

When the manual mode M is selected, the frame rate, the number of channels, and the number of lines may be directly set using the first priority setter 26 and the second priority setter 27 of the ultrasound probe 1, and the measurement depth may be directly set using the measurement depth adjuster 29.

The still image mode is the mode in which a still image, for example, a still image which is used for strict observation, strict diagnosis, or the like is acquired.

Next, the operation of the ultrasound diagnostic apparatus according to Embodiment 1 of the invention will be described.

First, the operator sets the measurement depth. With regard to the setting of the measurement depth, the operator may select the manual mode M and may directly set the measurement depth or the measurement mode may be selected by the measurement mode selector 28 of the ultrasound probe 1 to determine the measurement site, thereby indirectly setting the measurement depth.

If the operator abuts the head portion 21 of the ultrasound probe 1 and measurement of a diagnosis target site starts, first, ultrasonic waves are transmitted from a plurality of transducers 3 in response to the activation signals supplied from the transmission drive 7. The reception signal output from each transducer 3 having received an ultrasonic echo from the subject is supplied to the corresponding reception signal processor 4 to produce sample data. Sample data is converted to serial sample data by the parallel/serial converter 5, and transmitted from the wireless communication unit 6 to the diagnostic apparatus body 2 in a wireless manner. Sample data received by the wireless communication unit 13 of the ultrasound diagnostic apparatus body 2 is converted to parallel sample data by the serial/parallel converter 14 and stored in the data storage unit 15. Sample data for one frame is read from the data storage unit 15, an image signal is produced by the image producer 16, and an ultrasound diagnostic image is displayed on the monitor 18 on the basis of the image signal by the display controller 17.

In the ultrasound diagnostic apparatus which performs such an operation, power consumption when the ultrasound probe 1 is intermittently operated, the frame rate, the number of lines, the number of channels, and the measurement depth have the following relationship:

power consumption ∝ frame rate×the number of lines×the number of channels×measurement depth Power consumption in the ultrasound probe 1 is mainly due to a circuit which is used to transmit ultrasonic waves to the transducers 3, a circuit which performs signal processing after an ultrasonic echo is received by the transducers 3, and the wireless communication unit 6 which transmits the acquired signal to the ultrasound diagnostic apparatus body 2. That is, as ultrasonic waves are transmitted from and received by the transducers 3 and a large number of signals are acquired, power consumption in the ultrasound probe 1 increases.

The above-described relationship of power consumption will be described focusing on the number of transducers to be actuated. Since the number of channels represents the number of transducers which are used to acquire a single scan line, in order to acquire a single ultrasound image, a number of transducers corresponding to the number of lines×the number of channels are actuated. Since the frame rate represents the number of ultrasound images to be acquired per unit time, the increase in frame rate increases the number of transducers to be actuated by multiplication of the number of lines×the number of channels. Accordingly, power consumption increases in proportion to the number of lines×the number of channels×frame rate. The measurement depth affects the time for which the transducers or the like are actuated, and as the measurement depth increases, the transducers or the like needs to be actuated for an increased length of time. As the transducers are actuated for an increased length of time, power consumption increases, so that the measurement depth affects power consumption by multiplication.

Although as power consumption increases, the ultrasound probe 1 generates more heat, heat is dissipated from the surface of the ultrasound probe 1. For this reason, if the amount of heat generation and the amount of heat dissipation are balanced, the surface temperature of the ultrasound probe 1 is maintained at a predetermined temperature. Since there is a limit that the surface temperature of the ultrasound probe 1 should be equal to or lower than 43° C., it is necessary to suppress power consumption in the ultrasound probe 1 to be equal to or lower than a given value, and to suppress the amount of heat generation of the ultrasound probe 1 to be equal to or smaller than the amount of heat dissipation.

From the relational expression relating to power consumption, either of the frame rate, the number of lines, the number of channels, or the measurement depth is suppressed, thereby suppressing power consumption to be equal to or lower than a predetermined value. However, the fact that the measurement depth is approximately determined by the measurement site makes it impossible to adjust the measurement depth to suppress power consumption.

From among the frame rate, the number of channels, and the number of lines as the remaining measurement parameters affecting power consumption, the frame rate is the measurement parameter relating to temporal resolution of the ultrasound image, and the number of lines and the number of channels are the parameters relating to spatial resolution of the ultrasound image. However, if temporal resolution is suppressed, the frame rate is lowered, screen switching is visually perceived, and an unsatisfactory moving image is obtained. For this reason, it is difficult to follow the fast movement of the measurement target site, such as heart. If spatial resolution is suppressed, the number of lines or the number of channels concerning image quality is lowered, and the fine structure of the measurement target site is not accurately obtained, thereby affecting diagnosis. In order to reduce power consumption, if the frame rate, the number of lines, and the number of channels are reduced uniformly, it is difficult to set an optimum measurement parameter for the operator when observing an ultrasound image, making it difficult to obtain an optimum ultrasound image according to a site under diagnosis or a diagnosis object, for example, an ultrasound image for diagnosis having a desired frame rate and/or desired image quality as the operator desires.

Accordingly, in the ultrasound diagnostic apparatus according to Embodiment 1 of the invention, the first priority setter 26 and the second priority setter 27 are provided in the ultrasound probe 1 to set the priorities of the measurement parameters.

For example, when the measurement site is heart, the heart mode is set as the measurement mode, and the measurement depth is 15 cm, allowable power consumption of the ultrasound probe 1 is limited to a predetermined value (4 W) defined by the configuration of the ultrasound probe 1 such that the surface temperature of the ultrasound probe 1 is, for example, equal to or lower than 43° C.

In the invention, the upper limit value of power consumption such that the surface temperature of the ultrasound probe 1 does not exceed a predefined value, for example, 43° C. is referred to as allowable power consumption. Power consumption in the ultrasound probe 1 is mainly power consumption due to the transducers 3, the parallel/serial converter 5, the wireless communication unit 6, the transmission drive 7, the probe controller 11, and the like. At this time, if temporal resolution and spatial resolution are given the same priority in the first priority setter 26, and if the number of lines and the number of channels are given the same priority in the second priority setter 27, the frame rate is 30 fps, the number of lines is 64, and the number of channels is 32 channels. Unless the ultrasound probe 1 is actuated with these measurement parameters, power consumption is equal to or lower than the predetermined value, and the surface temperature of the ultrasound probe 1 does not exceed the predefined value (43° C.)

In this case, when the operator wants to give preference to temporal resolution, the first priority setter 26 is rotated to the right. When the operator rotates the first priority setter 26, and the priority ratio of temporal resolution and spatial resolution is set to, for example, 1:2, the probe controller 11 calculates the values of the measurement parameters in accordance with the set priorities. In this case, with regard to the values of the measurement parameters, it should suffice that the frame rate is 15 fps, the number of lines is 90, and the number of channels is 45 channels. That is, since the performance of temporal resolution is given preference over spatial resolution, the performance of temporal resolution is improved, while the performance of spatial resolution is suppressed. However, since the total power consumption is not changed, even when the ultrasound probe 1 is actuated with the measurement parameters, the surface temperature of the ultrasound probe 1 never exceeds the predefined value (43° C.)

When the priority ratio of temporal resolution and spatial resolution is 1:2, and for example, when the operator wants to give preference to the number of lines over the number of channels, the second priority setter 27 can be rotated to the right to give preference to the number of lines. In this case, the frame rate is 15 fps, the number of lines is 128, and the number of channels is 32 channels. In this case, since the total power consumption is not changed, even when the ultrasound probe 1 is actuated with the measurement parameters, the surface temperature of the ultrasound probe 1 never exceeds the predefined value (43° C.)

When the operator adjusts the measurement depth using the measurement depth adjuster 29, the setting of the adjusted measurement depth is given preference over the settings of the frame rate, the number of channels, and the number of lines. Accordingly, the values of the frame rate, the number of channels, and the number of lines are set in accordance with the priorities such that power consumption is equal to or lower than allowable power consumption after the adjustment of the measurement depth.

As described above, in the ultrasound diagnostic apparatus according to Embodiment 1 of the invention, the first priority setter 26 which sets which of temporal resolution and spatial resolution is given preference and the priority, and the probe controller 11 which sets the measurement parameters in accordance with the priority set by the first priority setter 26 and the measurement depth set in advance such that power consumption is equal to or lower than allowable power consumption, and controls the operations of the respective units of the ultrasound probe 1 are provided in the ultrasound probe 1. Therefore, it becomes possible for the operator to set whether to obtain an ultrasound image having preference on temporal resolution or to obtain an ultrasound image having preference on spatial resolution in accordance with a site under diagnosis or a diagnosis object while suppressing heat generation in the ultrasound probe 1 to be equal to or smaller than a predetermined value.

According to Embodiment 1, from among the measurement parameters relating to spatial resolution, the second priority setter 27 which sets which of the number of lines and the number of channels is given preference and the priority is provided, making it possible for the operator to set which of the two measurement parameters relating to spatial resolution is given preference and the priority.

Embodiment 2

FIG. 3 is a block diagram of an ultrasound diagnostic apparatus according to Embodiment 2 of the invention. An ultrasound diagnostic apparatus according to Embodiment 2 of the invention includes an ultrasound probe 40 and an ultrasound diagnostic apparatus 2. The ultrasound diagnostic apparatus of Embodiment 2 shown in FIG. 3 has the same configuration as the ultrasound diagnostic apparatus of Embodiment 1 shown in FIG. 1, except that the ultrasound probe 40 includes a temperature sensor 41, a probe controller 42, and a measurement mode selector 43, compared to the ultrasound probe 1. For this reason, the same components as those in Embodiment 1 are represented by the same reference numerals, and description thereof will not be repeated.

The ultrasound probe 40 has a plurality of ultrasound transducers 3, a plurality of reception signal processors 4 which are provided to correspond to the transducers 3, a parallel/serial converter 5, a wireless communication unit 6, a transmission drive 7, a transmission controller 8, a reception controller 9, a communication controller 10, a probe controller 42, a first priority setter 26, a second priority setter 27, a measurement depth adjuster 29, a display controller 30, a monitor 31, a temperature sensor 41, and a measurement mode selector 43. The ultrasound probe 40 shown in FIG. 3 is the same as the ultrasound probe 1 shown in FIG. 1, except that, instead of the probe controller 11 and the measurement mode selector 28 of the ultrasound probe 1, the temperature sensor 41, the probe controller 42, and the measurement mode selector 43 are provided. For this reason, description will be mainly provided focusing on the differences.

The temperature sensor 41 is a sensor which measures the surface or internal temperature of the ultrasound probe 40. The temperature sensor 41 outputs the surface or internal temperature of the ultrasound probe 40 to the probe controller 42.

As the temperature sensor 41, any sensor may be used insofar as the sensor can measure the surface or internal temperature of the ultrasound probe 40. A known temperature sensor may be used.

The probe controller 42 has the same configuration and functions as the probe controller 11 of Embodiment 1, except that, in a mode B described below, allowable power consumption is variable depending on the surface or internal temperature of the ultrasound probe 40 measured by the temperature sensor 41, and thus description thereof will not be repeated.

Similarly to the measurement mode selector 28, the measurement mode selector 43 is a rotating dial, and can select a mode A in which allowable power consumption is set in advance and a mode B in which the value of allowable power consumption is variable depending on the surface or internal temperature of the ultrasound probe 40. In each mode, the measurement mode of the measurement mode selector 28 in Embodiment 1 can be selected.

The details of the mode A and the mode B which are selected by the measurement mode selector 43 will be described below.

Figure 4:
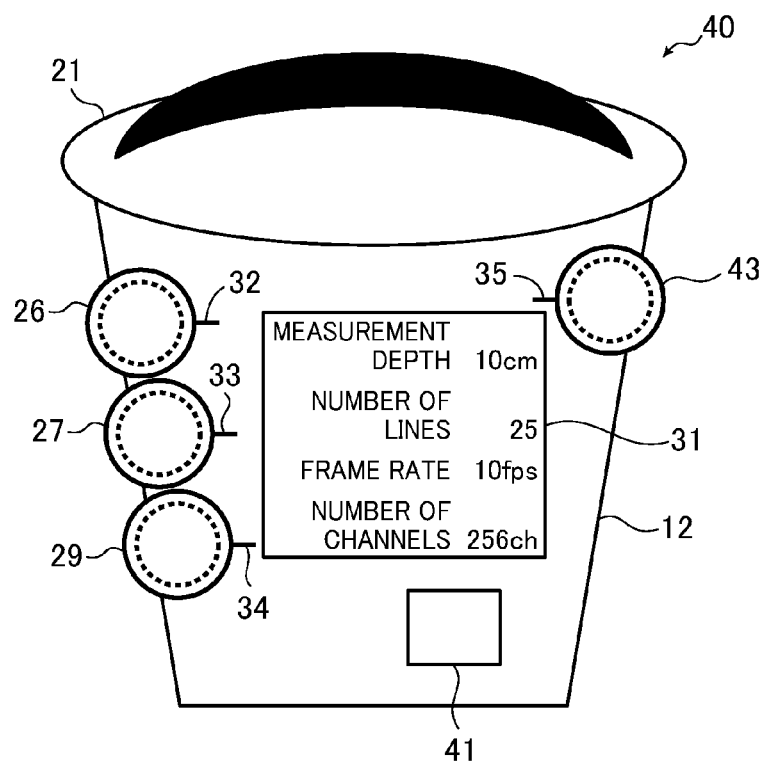
FIG. 4 is an appearance diagram of an ultrasound probe of the ultrasound diagnostic apparatus shown in FIG. 3.

FIG. 4 is an appearance diagram of the ultrasound probe 40 of the ultrasound diagnostic apparatus shown in FIG. 3.

As shown in FIG. 4, the temperature sensor 41 is attached to the surface of a housing 12 of the ultrasound probe 40, and measures the surface temperature of the ultrasound probe 40. In this embodiment, the temperature sensor 41 may not be attached to the surface of the housing 12 of the ultrasound probe 40, and may be attached to the rear surface or inside of the housing 12 of the ultrasound probe 40. In this case, the temperature sensor 41 may be attached to a position where the temperature of the head portion 21 which abuts on a biological body can be mainly measured. In this way, the temperature sensor 41 can measure the surface or internal temperature of the ultrasound probe 40, and may mainly measure the temperature of the head portion 21 which abuts on the biological body.

As shown in FIG. 4, the measurement mode selector 43 is provided at a position facing the first priority setter 26 at the right end of FIG. 4. The position of the measurement mode selector 43 is not limited to the example of the drawing, and the measurement mode selector 43 may be provided at any position. As in Embodiment 1, it is preferable that the measurement mode selector 43 is provided at a position which is not touched when the operator grips the grip portion 12.

Next, the operation of the ultrasound diagnostic apparatus according to Embodiment 2 of the invention will be described.

The operation in Embodiment 2 is the same as the operation in Embodiment 1, except for operations specific to a mode A and a mode B, and description of the same operation will not be provided. Description will be mainly provided as to the operation relating to the mode A and the operation relating to the mode B.

The mode A is the mode in which allowable power consumption is set in advance. The operation in the mode A of the ultrasound diagnostic apparatus of Embodiment 2 is the operation of the ultrasound diagnostic apparatus of Embodiment 1, except for a selection operation of the mode A by the measurement mode selector 43, and thus description of a subsequent operation will not be repeated.

In the ultrasound probe 40 of the ultrasound diagnostic apparatus of Embodiment 2, if the mode A is selected by the measurement mode selector 43, and a measurement site is selected as a mode, similarly to the ultrasound probe 1 shown in FIG. 1, the measurement depth (initial depth) which is set by default by the measurement depth adjuster 29 is adjusted, and the priorities are set by the first priority setter 26 and the second priority setter 27. In the probe controller 42, with regard to the measurement depth adjusted by the measurement depth adjuster 29, the measurement parameters are set such that power consumption is equal to or lower than allowable power consumption in accordance with the priorities set by the first priority setter 26 and the second priority setter 27.

In the mode A, the operator may set allowable power consumption of the ultrasound probe 40 in advance, and the maximum value of the surface temperature of the ultrasound probe 40, instead of allowable power consumption, may be set. If the maximum value of the surface temperature of the ultrasound probe 40 is set, the maximum value of possible power consumption in the ultrasound probe 40 is determined and set.

The mode B is the mode in which allowable power consumption is variable depending on the surface or internal temperature (in the following description, representatively referred to as surface temperature) of the ultrasound probe 40.

In the operation in the mode B of the ultrasound diagnostic apparatus of Embodiment 2, the operator initially sets the measurement depth. With regard to the setting of the measurement depth, the operator may directly set the measurement depth, or the operator may select a measurement site to set the measurement depth. With regard to the direct setting of the measurement depth by the operator, data of the measurement depth input using the operating unit 22 of the ultrasound diagnostic apparatus body 2 shown in FIG. 3 may be transmitted to the ultrasound probe 40 through the apparatus body controller 20, the communication controller 19, and the wireless communication unit 13. In the ultrasound probe 40, data may be received by the wireless communication unit 6 and transmitted to the probe controller 42 through the communication controller 10. In the mode B, the measurement depth may be directly set by the measurement depth adjuster 29, and in the mode B, a measurement site may be selected as a mode by the measurement mode selector 43.

Subsequently, the surface temperature of the ultrasound probe 40 is measured by the temperature sensor 41. The probe controller 42 determines allowable power consumption on the basis of the surface temperature of the ultrasound probe 40 measured by the temperature sensor 41. The surface temperature of the ultrasound probe 40 measured by the temperature sensor 41 may be displayed on the monitor 31.

Figure 5:
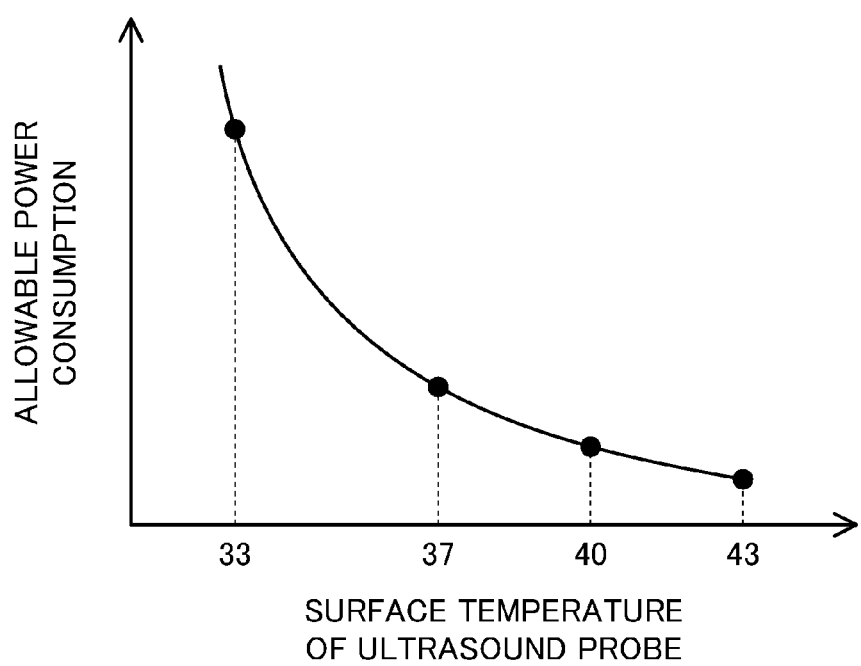
FIG. 5 is a graph showing the relationship between the temperature of the surface of the ultrasound probe and allowable power consumption.

An example of allowable power consumption with respect to the surface temperature of the ultrasound probe 40 is shown in a graph of FIG. 5. The surface temperature of the ultrasound probe 40 and allowable power consumption have an inverse relationship. That is, as the surface temperature of the ultrasound probe 40 increases, allowable power consumption decreases. Specifically, when the surface temperature of the ultrasound probe 40 is 33° C., even if heat is somewhat generated, there is no problem. For this reason, allowable power consumption is limited to a slightly large first predetermined value (7 W) which is defined by the configuration of the ultrasound probe 40. When the surface temperature of the ultrasound probe 40 is 37° C., allowable power consumption is limited to a second predetermined value (6 W) which is defined by the configuration of the ultrasound probe 40 and smaller than the first predetermined value such that the surface temperature of the ultrasound probe 40 does not rapidly increase. When the surface temperature of the ultrasound probe 40 is 40° C., allowable power consumption is limited to a third predetermined value (5 W) which is defined by the configuration of the ultrasound probe 40 and smaller than the second predetermined value such that the surface temperature of the ultrasound probe 40 does not increase any more. When the surface temperature of the ultrasound probe 40 is equal to or higher than 43° C., the operation of the ultrasound probe 40 is stopped.

The values of the frame rate, the number of channels, and the number of lines set by the probe controller 42 are changed due to a change in allowable power consumption with a change in the surface temperature of the ultrasound probe 40. In this case, changes in the values of the frame rate, the number of channels, and the number of lines are determined on the basis of the priorities set by the first priority setter 26 and the second priority setter 27. For example, when the surface temperature of the ultrasound probe 40 increases in a state where the frame rate, the number of channels, and the number of lines have the same priority, and allowable power consumption decreases, the probe controller 42 decreases the values of the frame rate, the number of channels, and the number of lines in equal proportion such that power consumption does not exceed decreased allowable power consumption. When the surface temperature of the ultrasound probe 40 increases in a state where the frame rate, the number of channels, and the number of lines do not have the same priority, and allowable power consumption decreases, the probe controller 42 decreases the values of the frame rate, the number of channels, and the number of lines in accordance with the priorities such that power consumption does not exceed decreased allowable power consumption. At this time, the value of a measurement parameter having low priority decreases in great proportion.

As described above, in the ultrasound diagnostic apparatus according to Embodiment 2 of the invention, the mode A in which allowable power consumption is set in advance and the mode B in which the value of allowable power consumption is variable depending on the surface or internal temperature of the ultrasound probe are provided, and the operator can select a preferred measurement mode.

In the mode A, since allowable power consumption is set in advance, as in Embodiment 1, the operator can adjust the measurement depth without taking into consideration, that is, without being conscious of allowable power consumption or the surface or internal temperature of the ultrasound probe, and can set the optimum values of the frame rate, the number of channels, and the number of lines.

In the mode B, the optimum values of the frame rate, the number of channels, and the number of lines are set in accordance with the surface or internal temperature of the ultrasound probe 40. For this reason, for example, when the surface temperature of the ultrasound probe 40 is low, the values of the frame rate, the number of channels, and the number of lines can be set to be high compared to a case where allowable power consumption is not variable.

In this embodiment, it is not necessary that the measurement mode selector 43 can select both modes of the mode A and the mode B, and only either mode may be selected.

In the foregoing embodiments, the priority of each measurement parameter may be determined in advance depending on a measurement site. For example, when a measurement site is heart, since the movement is fast, the priority of the frame rate (temporal resolution) is set to be relatively high.

In the foregoing embodiments, the first priority setter 26 and the second priority setter 27 may not be provided. For example, when the operator wants to set the priorities of spatial resolution and temporal resolution, only the first priority setter 26 may be provided.

The first priority setter 26 and the second priority setter 27 are provided in the ultrasound probe 1 or 40, and may be provided in the ultrasound diagnostic apparatus body 2. The first priority setter 26 and the second priority setter 27 may be provided in both the ultrasound probe 1 or 40 and the ultrasound diagnostic apparatus body 2. For example, like the settings of the priorities of temporal resolution and the number of channels, other combinations of measurement parameters having priority may be used. Three or more priority setters may be provided.

Although in the foregoing embodiments, the first priority setter 26 and the second priority setter 27 are rotating dials, there may be no need for these input devices. For example, priority may be selected by an input device, such as a switch, or a numerical value may be entered to directly designate priority.

In the foregoing embodiments, the settings of the measurement parameters according to the priorities set by the ultrasound probe 1 or 40, or the adjustment of the measurement depth may not be performed by the probe controller 11 of the ultrasound probe 1 or 40. For example, the priorities set by the first priority setter 26 and the second priority setter 27 or the measurement depth adjusted by the measurement depth adjuster 29 may be output to the ultrasound diagnostic apparatus body 2 through the probe controller 11, the communication controller 10, and the wireless communication unit 6. In the ultrasound diagnostic apparatus body 2, the priorities or the measurement depth may be received by the wireless communication unit 13 and transmitted to the apparatus body controller 20 through the communication controller 19. In the apparatus body controller 20, the measurement parameters may be set on the basis of the adjusted measurement depth and the set priorities. In this case, the measurement parameters set by the apparatus body controller 20 of the ultrasound diagnostic apparatus body 2 are output to the ultrasound probe 1 or 40 and transmitted to the probe controller 11 through a transmission path opposite to the above-described transmission path. In the probe controller 11, the operations of the respective units of the ultrasound probe 1 or 40 are controlled using the measurement parameters output from the ultrasound diagnostic apparatus body 2.

In the foregoing embodiments, the monitor 31 which displays the measurement depth or the measurement parameters may not be provided in the ultrasound probe 1 or 40, and the measurement depth or the measurement parameters may be displayed on only the monitor 18 of the ultrasound diagnostic apparatus body 2.

The measurement parameters which can be given priority are not limited to the measurement parameters relating to temporal resolution and spatial resolution, or the frame rate, the number of channels, and the number of lines described in the foregoing embodiments, and may be a piezoelectric element actuation voltage and an ADC sampling frequency.

In the foregoing embodiments, the measurement mode selector 28 and 43 may not be provided in the ultrasound probe 1 and 40, and may be provided in the ultrasound diagnostic apparatus body 2. The measurement depth adjuster 29 may not be provided in the ultrasound probe 1 or 40, and may be provided in the ultrasound diagnostic apparatus body 2.

In the foregoing embodiments, the ultrasound probe 1 or 40 and the ultrasound diagnostic apparatus body 2 may not perform wireless communication, and may be connected together by a wire, such as a cable.

The ultrasound diagnostic apparatus of each embodiment may be installed in a room or the like of a hospital or the like, may be of a mobile type installed or placed on a cart or the like, or may be of an externally portable type.

Although the ultrasound probe and the ultrasound diagnostic apparatus of the invention have been described in detail in connection with various embodiments, the invention is not limited to the foregoing embodiments, and various improvements or changes may be made without departing from the gist of the invention.

What is claimed is:

1. An ultrasound probe which transmits a transmission signal produced through a signal process on a reception signal, which is acquired by transmitting ultrasonic waves toward a subject and receiving an ultrasonic echo reflected from a measurement site of a subject, to an apparatus body of an ultrasound diagnostic apparatus, which produces an ultrasound diagnostic image from the transmission signal, the ultrasound probe comprising:
   a first priority setter configured to set a first priority regarding which of a first measurement parameter relating to temporal resolution and a second measurement parameter relating to spatial resolution when acquiring the reception signal to produce the ultrasound diagnostic image is given preference;
   a probe controller configured to set values of the first and second measurement parameters in accordance with allowable power consumption set in advance in accordance with heat generation associated with a process including the signal process, a measurement depth set in accordance with the measurement site of the subject, and the first priority set by the first priority setter, and to control transmission and reception operations based on the set first and second measurement parameters.

2. The ultrasound probe according to claim 1, wherein the probe controller sets the values of the first and second measurement parameters in accordance with the measurement depth and the first priority such that power consumption falls within the allowable power consumption.

3. The ultrasound probe according to claim 1, wherein the first measurement parameter is a frame rate when acquiring the reception signal to produce the ultrasound diagnostic image, and
   the second measurement parameter is a number of scan lines for producing the ultrasound diagnostic image and a number of channels of transmission and reception of the ultrasonic waves.

4. The ultrasound probe according to claim 3, further comprising:
   a second priority setter configured to set a second priority regarding which of the number of scan lines and the number of channels included in the second measurement parameter relating to the spatial resolution is given preference,
   wherein the probe controller sets values of the number of scan lines and the number of channels in accordance with a set value of the second measurement parameter and the second priority set by the second priority setter.

5. The ultrasound probe according to claim 3, further comprising:
   a monitor which displays at least one of the first measurement parameter, the second measurement parameter, the measurement depth, the frame rate, the number of scan lines, and the number of channels.

6. The ultrasound probe according to claim 1, further comprising:
   a measurement depth adjuster configured to set, with the measurement depth set in advance for the measurement site of the subject as an initial depth, an adjustment amount to adjust the measurement depth to a deeper side than the initial depth or an adjustment amount to adjust the measurement depth to a shallower side than the initial depth,
   wherein the probe controller further sets the adjusted measurement depth in accordance with the initial depth set in advance and the adjustment amount set by the measurement depth adjuster.

7. The ultrasound probe according to claim 1, wherein the priority setter is a rotating dial.

8. The ultrasound probe according to claim 1, further comprising:
   a grip portion which is gripped by an operator; and
   a head portion which abuts on the subject and irradiates the ultrasonic waves,
   wherein the priority setter is provided at a position, excluding the grip portion and the head portion, at which the operator does not grip.

9. The ultrasound probe according to claim 1, further comprising:
   a measurement mode selector configured to select a measurement mode of the subject.

10. The ultrasound probe according to claim 1, wherein the measurement mode includes a mode in which at least one measurement site is measured and/or a still image of the ultrasound diagnostic image is produced.

11. The ultrasound probe according to claim 1, further comprising:
    a temperature sensor which measures an internal temperature or a surface temperature of the ultrasound probe,
    wherein the probe controller further changes a value of the allowable power consumption set in advance based on the internal temperature or the surface temperature measured by the temperature sensor.

12. An ultrasound diagnostic apparatus comprising:
    the ultrasound probe according to claim 1; and
    an ultrasound diagnostic apparatus body which produces the ultrasound diagnostic image,
    wherein the ultrasound probe further has
    ultrasound transducers configured to transmit the ultrasonic waves toward the subject, to receive the ultrasonic echo reflected from the subject, and to output the reception signal,
    a signal processor which performs the signal process on the reception signal output from the ultrasound transducers to produce the transmission signal, and
    a first communicator configured to transmit the transmission signal produced by the signal processor to the ultrasound diagnostic apparatus body which produces the ultrasound diagnostic image from the transmission signal, and
    the ultrasound diagnostic apparatus body has a second communicator configured to receive the transmission signal from the first communicator of the ultrasound probe, an image processor which produces the ultrasound diagnostic image based on the transmission signal received by the second communicator, and a monitor which displays the ultrasound diagnostic image produced by the image processor.

13. The ultrasound diagnostic apparatus according to claim 12,
wherein
the first communicator of the ultrasound probe is a first wireless communicator which transmits the transmission signal to the ultrasound diagnostic apparatus body in a wireless manner, and the second communicator is a second wireless communicator which receives the transmission signal from the first wireless communicator of the ultrasound probe in a wireless manner.

14. The ultrasound diagnostic apparatus according to claim 12,
wherein the monitor of the ultrasound diagnostic apparatus body further displays at least one of the measurement depth, the first measurement parameter, the second measurement parameter, a frame rate as the first measurement parameter, and the number of scan lines and the number of channels included in the second measurement parameter.

15. An ultrasound diagnostic apparatus comprising:
an ultrasound diagnostic apparatus body which produces an ultrasound diagnostic image; and
an ultrasound probe which transmits and receives ultrasonic waves to produce the ultrasound diagnostic image,
wherein the ultrasound probe has
ultrasound transducers configured to transmit the ultrasonic waves toward a subject, to receive an ultrasonic echo reflected from the subject, and to output a reception signal,
a signal processor which performs a signal process on the reception signal output from the ultrasound transducers to produce a transmission signal,
a first priority setter configured to set a first priority regarding which of a first measurement parameter relating to temporal resolution and a second measurement parameter relating to spatial resolution when acquiring the reception signal to produce the ultrasound diagnostic image is given preference, a probe controller configured to control operations of the ultrasound transducers, and a first communicator configured to transmit the transmission signal produced by the signal processor and the first priority set by the first priority setter to the ultrasound diagnostic apparatus body, and to receive data from the ultrasound diagnostic apparatus body, the ultrasound diagnostic apparatus body has
a second communicator configured to receive the transmission signal and the first priority from the first communicator of the ultrasound probe, and to transmit data to the first communicator of the ultrasound probe, an image processor configured to produce the ultrasound diagnostic image based on the transmission signal received by the second communicator, a monitor which displays the ultrasound diagnostic image produced by the image processor, and an apparatus body controller configured to set values of the first and second measurement parameters in accordance with the first priority set by the first priority setter of the ultrasound probe and received by the second communicator, allowable power consumption set in advance in accordance with heat generation associated with the operation of the ultrasound probe, and a measurement depth set in accordance with the measurement site of the subject by the ultrasound probe, wherein the second communicator of the ultrasound diagnostic apparatus body transmits the values of the first and second measurement parameters set by the apparatus body controller to the first communicator of the ultrasound probe as data, the first communicator of the ultrasound probe receives the values of the first and second measurement parameters as data, and the probe controller of the ultrasound probe controls the operation of the ultrasound transducers of the ultrasound probe based on the values of the first and second measurement parameters received by the first communicator and set by the apparatus body controller.

16. The ultrasound diagnostic apparatus according to claim 15,
wherein the first communicator of the ultrasound probe and the second communicator of the ultrasound diagnostic apparatus body are wireless communicators which perform wireless communication.

* * * * *